US012680115B2

(12) United States Patent
Stutzman

(10) Patent No.: US 12,680,115 B2
(45) Date of Patent: Jul. 14, 2026

(54) BIOGAS COLLECTION APPARATUS AND METHOD OF USE

(71) Applicant: Nicholas Stutzman, Tabor, SD (US)

(72) Inventor: Nicholas Stutzman, Tabor, SD (US)

( * ) Notice: Subject to any disclaimer, the term of this patent is extended or adjusted under 35 U.S.C. 154(b) by 419 days.

(21) Appl. No.: 18/214,190

(22) Filed: Jun. 26, 2023

(65) Prior Publication Data

US 2024/0425887 A1     Dec. 26, 2024

(51) Int. Cl.
| | |
|---|---|
| *C12P 5/02* | (2006.01) |
| *A01K 1/00* | (2006.01) |
| *A01K 1/01* | (2006.01) |
| *C12M 1/00* | (2006.01) |
| *C12M 1/107* | (2006.01) |

(52) U.S. Cl.
CPC ............ *C12P 5/023* (2013.01); *A01K 1/0047* (2013.01); *C12M 21/04* (2013.01); *C12M 47/18* (2013.01); *A01K 1/01* (2013.01)

(58) Field of Classification Search
None
See application file for complete search history.

(56) References Cited

U.S. PATENT DOCUMENTS

| | | | | |
|---|---|---|---|---|
| 4,520,759 | A | 6/1985 | Deters | |
| 5,732,658 | A | 3/1998 | Wolters | |
| 5,911,195 | A | 6/1999 | Tripp | |
| 6,397,539 | B1 | 6/2002 | Kimura | |
| 7,186,339 | B1* | 3/2007 | Roos | A01C 3/023 |
| | | | | 210/603 |
| 7,293,529 | B2 | 11/2007 | Bauman | |
| 7,810,454 | B2 | 10/2010 | Boulant | |
| 2008/0289493 | A1 | 11/2008 | Caro | |
| 2014/0193898 | A1* | 7/2014 | Smith | C12N 1/12 |
| | | | | 47/62 A |
| 2016/0316712 | A1 | 11/2016 | Kratzer | |

\* cited by examiner

*Primary Examiner* — Blaine Lankford

(57) ABSTRACT

A biogas collection apparatus for nondilutive capturing of biogas includes a plurality of floats positionable upon waste in a waste collection pit of an animal production facility to maintain a piping network proximate to a surface level of the waste. The piping network is fluidic connectable to a biogas processor. A plurality of collectors is attached to and extends below the piping network. Closed tops of the collectors are in fluidic communication with the piping network and their open bottoms are positioned below the surface level. The collectors are arrayed in at different levels below the piping network. Gaps between collectors in one level are covered by collectors in the level above. Bubbles of biogas are collected by the collectors and the biogas is directed into the piping network while waste is free to pass between the collectors and into the waste collection pit.

18 Claims, 5 Drawing Sheets

BIOGAS COLLECTION APPARATUS AND METHOD OF USE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to gas collectors and more particularly pertains to a new gas collector for nondilutive capturing of biogas. Waste in a waste collection pit of an animal production facility, such as are used for the production of pigs, cows, poultry, or the like, produces biogas. Such animal production facilities typically are equipped with elaborate air handling systems, which pull and/or draw outside air into the animal production facilities. The air mixes with the biogas that is generated within the animal production facilities and is expelled therefrom, thereby reducing levels of biogas and potential for adverse outcomes to animals, humans, and the structures of the animal production facilities. Such adverse outcomes include detrimental health effects for the animals and the humans due to poisoning by constituents of the biogas, as well as injury to the animals and the humans and damage to the structures which may result from explosions of biogas. Systems that separate biogas from the biogas-air mixture that is expelled from the structures are known and can be installed in the animal production facilities. However, these systems are quite expensive, are difficult to install in existing animal production facilities, and typically require permits. The expense of the systems is driven, in part, by the costs for equipment to separate biogas that is highly diluted with air and by installation costs for anaerobic digesters.

(2) Description of Related Art Including Information Disclosed Under 37 CFR 1.97 and 1.98

The prior art relates to gas collectors but does not teach a biogas collection apparatus, as disclosed herein, wherein bubbles of biogas are collected beneath a surface level of waste in a waste collection pit of an animal production facility.

BRIEF SUMMARY OF THE INVENTION

An embodiment of the disclosure meets the needs presented above by generally comprising a plurality of floats, which is configured to be positioned upon waste in a waste collection pit of an animal production facility. A piping network is attached to the plurality of floats, which is configured to maintain the piping network proximate to a surface level of waste in the waste collection pit. The piping network is configured for fluidic connection to a biogas processor. A plurality of collectors is attached to and extends below the piping network. A closed top of each collector is in fluidic communication with the piping network. An open bottom of each collector is positioned below the surface level of the waste. The collectors are arrayed in a plurality of levels, with each level being positioned at a respective distance below the piping network. Each collector in a respective level is positioned over an associated gap that is defined by adjacently positioned collectors positioned below the collector. The collectors are configured to collect bubbles of biogas and to direct the biogas into the piping network. The collectors also are configured to allow for passage of waste into the waste collection pit.

Another embodiment of the disclosure includes a biogas collection system, which comprises an animal production facility, a biogas processor, and a biogas collection apparatus, according to the disclosure above. The animal production facility comprises a slotted floor upon which animals are held and a waste collection pit positioned beneath the slotted floor. The waste collection pit is configured to receive waste that is excreted by the animals upon passage of the waste through the slotted floor. The biogas collection apparatus is positioned in the waste collection pit and is operationally engaged to the biogas processor. The collectors operates as disclosed above to collect bubbles of biogas and to direct the biogas through the piping network to the biogas processor.

Yet another embodiment of the disclosure includes a method of collecting biogas, which entails provision of the biogas collection apparatus, according to the disclosure above. Steps of the method include positioning the biogas collection apparatus upon a surface of waste in a waste collection pit of an animal production facility, fluidically connecting the piping network to a biogas processor, waste passing through a slotted floor into the waste collection pit, microbial generation of biogas from the waste, collecting of bubbles of biogas by the collectors, and directing of the biogas through the piping network to the biogas processor.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
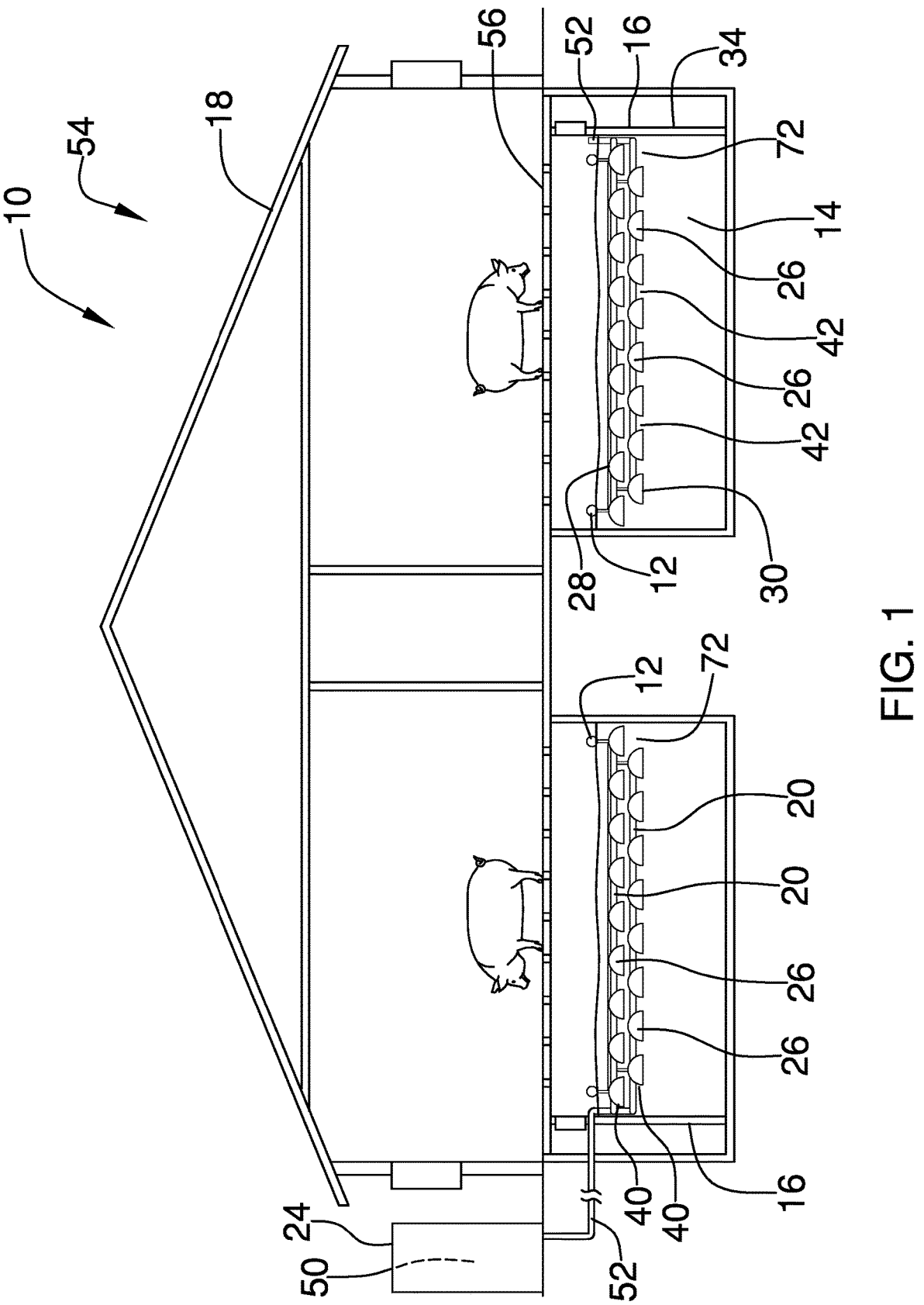
FIG. 1 is an end view of a biogas collection apparatus according to an embodiment of the disclosure.
Figure 2:
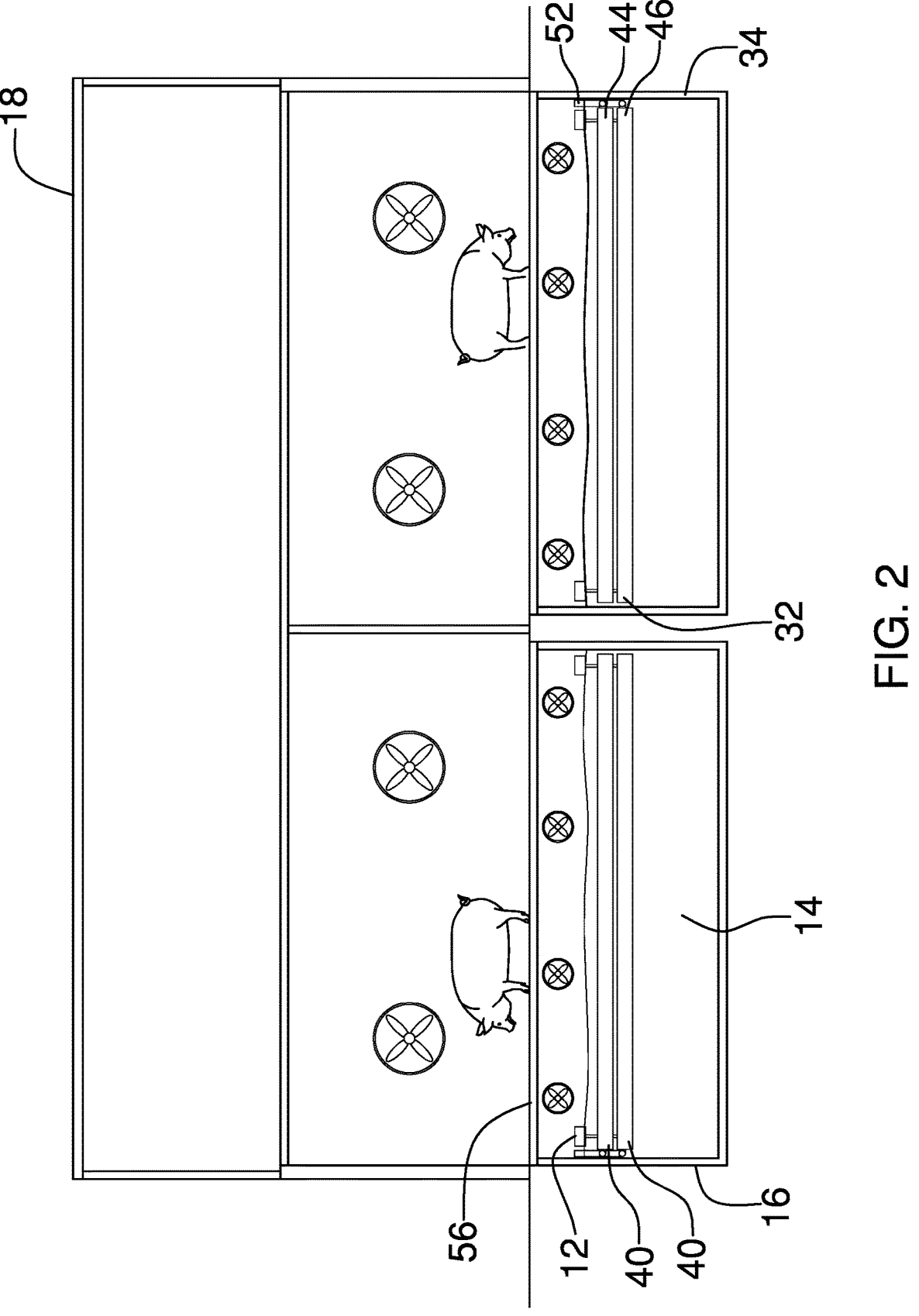
FIG. 2 is a side view of an embodiment of the disclosure.

With reference now to the drawings, and in particular to FIGS. 1 through 5 thereof, a new gas collector embodying the principles and concepts of an embodiment of the disclosure and generally designated by the reference numeral 10 will be described.

As best illustrated in FIGS. 1 through 5, the biogas collection apparatus 10 generally comprises a plurality of floats 12, which may comprise substantially rigid hollow members, resilient balloons, or the like. The floats 12 are configured to be positioned upon waste 14 in a waste collection pit 16 of an animal production facility 18, such as are used for the production of pigs, cows, poultry, or the like. A piping network 20, is attached to the plurality of floats 12, which is configured to maintain the piping network 20 proximate to a surface level 22 of waste 14 in the waste collection pit 16. The piping network 20 is configured for fluidic connection to a biogas processor 24. Biogas processor 24, in the context of this disclosure, should be interpreted to mean a biogas collection vessel, a biogas separator, a biogas purifier, a combination biogas separator-purifier, or the like, and is not intended to be limiting in any respect.

A plurality of collectors 26 is attached to and extends from the piping network 20. A closed top 28 of each collector 26 is in fluidic communication with the piping network 20. An open bottom 30 of each collector 26 is positioned below the surface level 22 of the waste 14. The plurality of collectors 26 is anticipated to have a circumference 32 that is complementary to that of a sidewall 34 of the waste collection pit 16 so that the plurality of collectors 26 substantially covers the entire surface of the waste 14 therein. The floats 12 rise and fall along with the surface level 22 of the waste 14, thereby maintaining the collectors 26 as required with their open bottoms 30 below the surface level 22. The surface level 22 of the waste 14 varies with the season and during pumping and emptying the waste collection pit 16, which typically would be performed once or twice per year.

Figure 3:
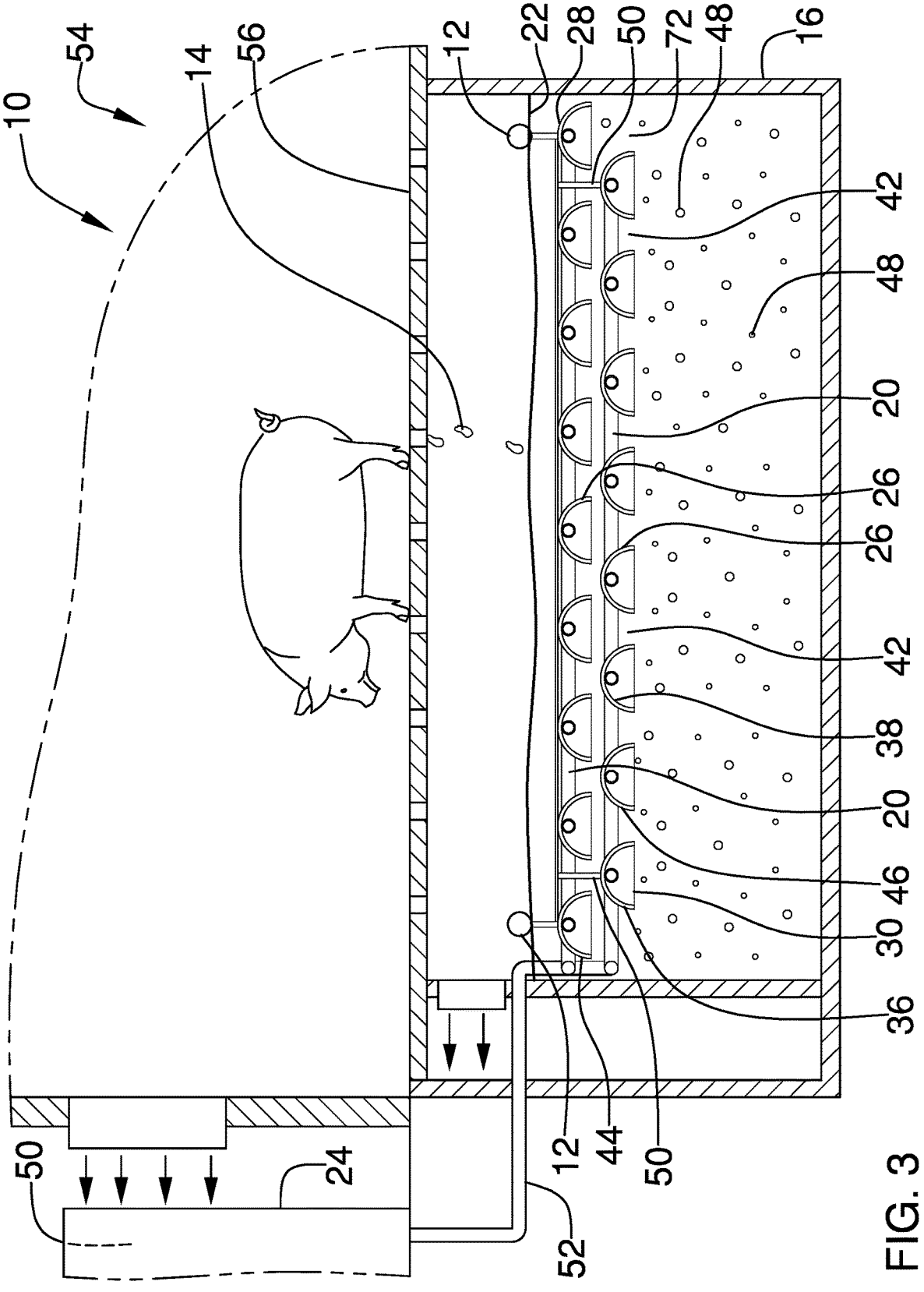
FIG. 3 is an end cross-sectional view of an embodiment of the disclosure.
Figure 4:
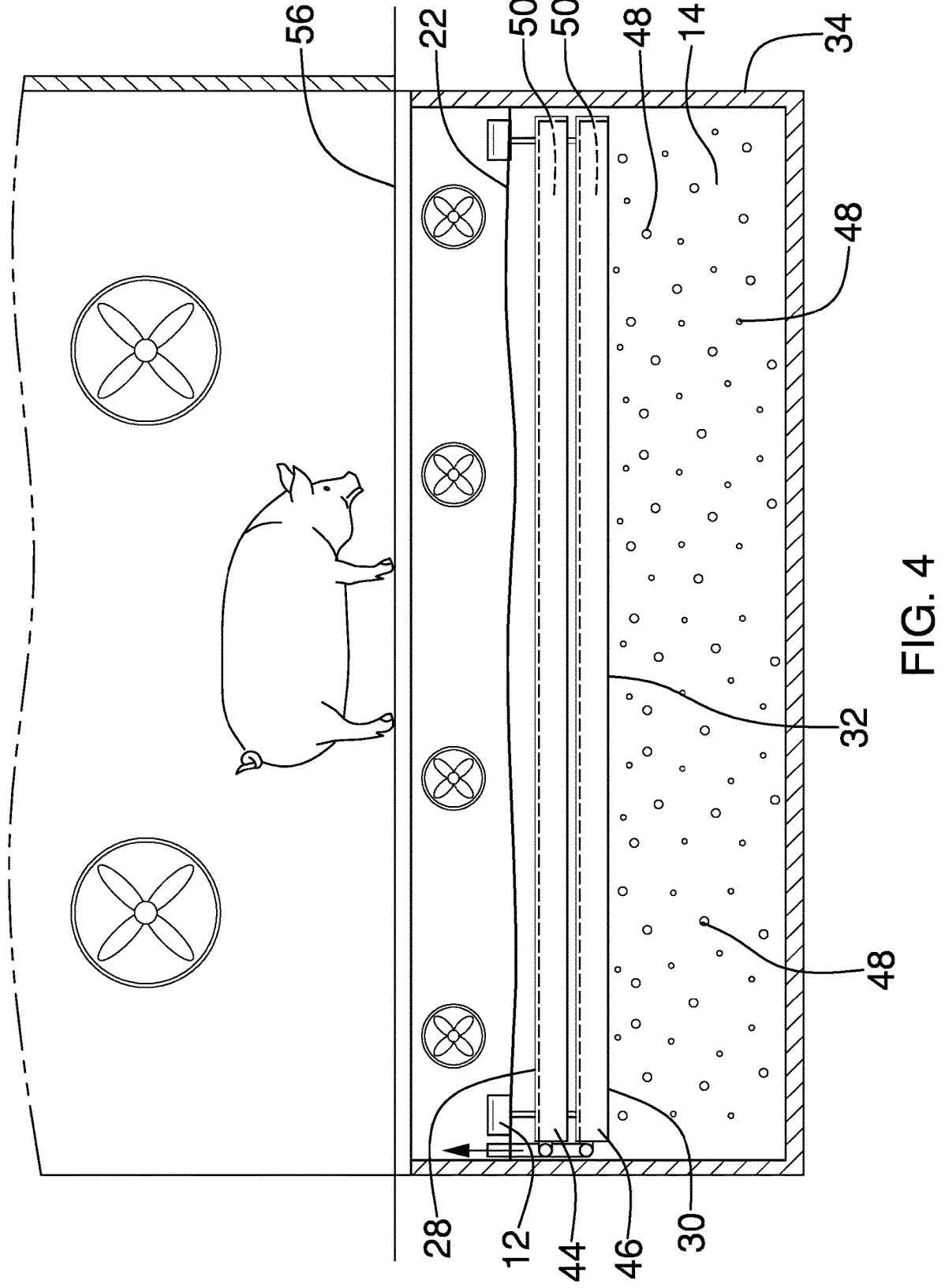
FIG. 4 is a side cross-sectional view of an embodiment of the disclosure.
Figure 5:
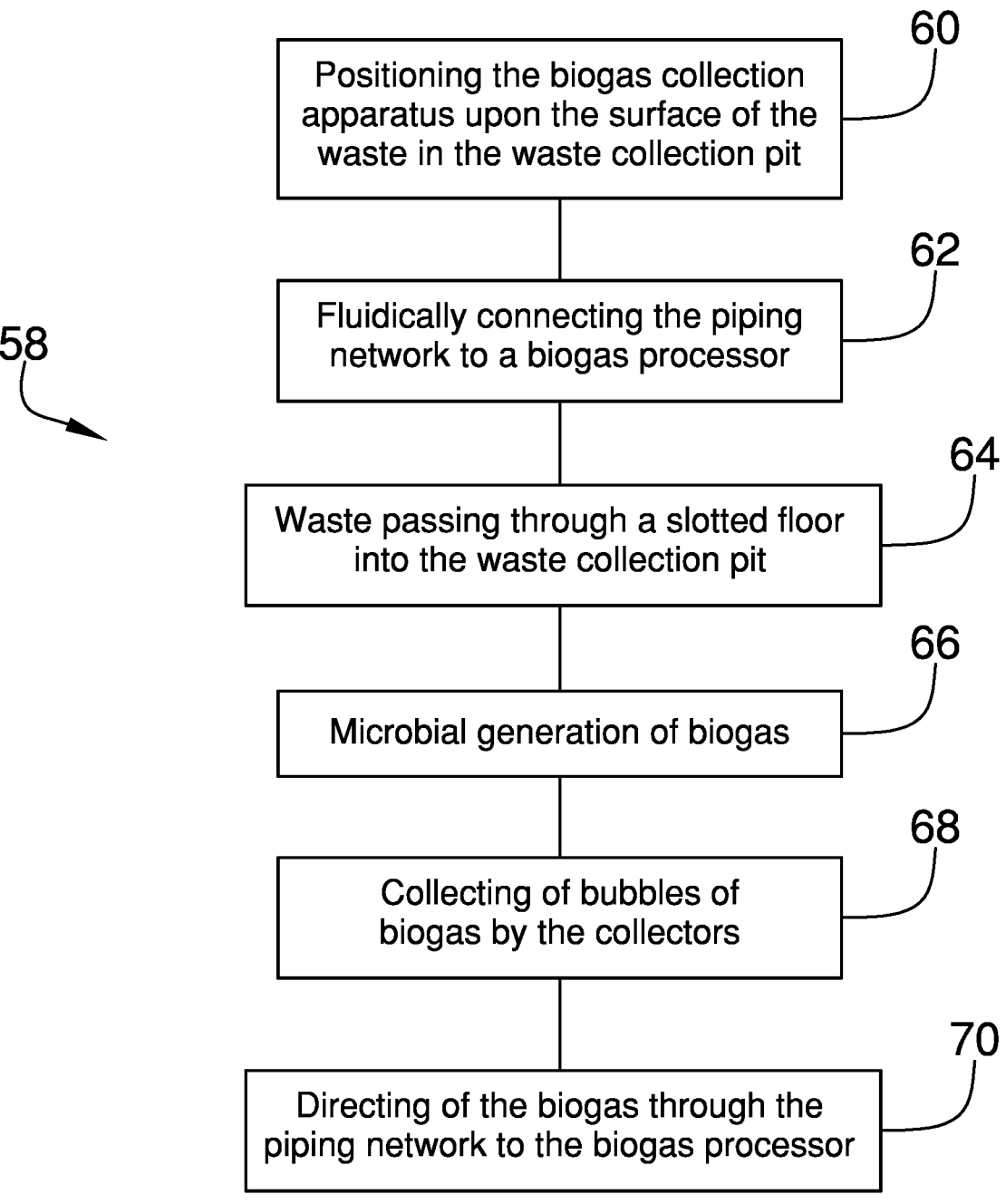
FIG. 5 is a flow diagram for a method utilizing an embodiment of the disclosure.

Each collector 26 may comprise an inverted trough 36, which has a cross-sectional profile 38 that is substantially semicircular, as is shown in FIG. 3. The present invention also anticipates the collector 26 being alternatively shaped, such as, but not limited to, frustum shaped, or the like. The collectors 26 of sufficient rigidity so as to maintain their shape and may be manufactured from plastic, aluminum, wood, or the like, or from combinations thereof. The piping network 20 comprises lightweight but substantially rigid piping, such as may be manufactured from plastic, aluminum, or the like. The piping network 20 thus provides a framework for attachment of the plurality of collectors 26 and serves to maintain relative positioning of each collector 26 relative to the other collectors 26. A plurality of cross braces 74 may be attached to the piping network 20 to stabilize the piping network 20.

The collectors 26 are arrayed in a plurality of levels 40, with each level 40 being positioned at a respective distance below the piping network 20. As is shown in FIGS. 1 and 3, each collector 26 in a respective level 40 is positioned over an associated gap 42 that is defined by adjacently positioned collectors 26 that are positioned below the collector 26. The plurality of levels 40 may comprise an upper level 44 and a lower level 46, with each collector 26 in the upper level 44 being positioned over the gap 42 defined by the adjacently positioned collectors 26 in the lower level 46. The present invention also anticipates one or more additional levels 40 of collectors 26 being positioned below the lower level 46. As is shown in FIGS. 1 and 3, the collector 26 in the upper level 44 and nearest to the sidewall 34 covers an opening 72 between the sidewall 34 and a collector 26 in the lower level 46.

The collectors 26 are configured to collect bubbles 48 of biogas 50 and to direct the biogas 50 into the piping network 20. With the open bottoms 30 of the collectors 26 being positioned below the surface level 22 of the waste 14, the biogas 50 is collected without impingement by air that is passing over the waste 14. Therefore, the biogas 50 is collected without being diluted. The present invention anticipates the piping network 20 being attached to an exhaust pipe 52, which is configured to be connectable to the biogas processor 24. Also anticipated by the present invention are one or both of a blower and a pump (not shown), which would be positioned in-line with the piping network 20 to facilitate movement of the biogas 50 to the biogas processor 24.

The collectors 26 also are configured to allow for passage of waste 14 into the waste collection pit 16. A distance between the open bottoms 30 of the collectors 26 in the upper level 44 and the closed tops 28 of the collectors 26 in the lower level 46 is sufficient to allow waste 14, in solid form, to pass between the collectors 26 and into the waste collection pit 16.

The biogas collection apparatus 10 may be configured so that, upon installation, the closed tops 28 of the collectors 26 in the upper level 44 are above the surface level 22 of the waste 14. In this circumstance, the cross-sectional profile 38 of the collectors 26 being semicircular allows for solids to be easily washed off of closed tops 28 of the collectors 26 in the upper level 44 as manure, urine, and water travel through the slotted floor 56 and into the waste collection pit 16.

The present invention anticipates the biogas collection apparatus 10 being modular and thus readily installable in existing waste collection pits 16, though new pits 16 may also be built to accommodate the apparatus 10. The biogas collection apparatus 10 is intended to provide an economical means for operators of animal production facilities 18 to access an additional revenue stream by capturing biogas 50. Additional benefits are potential reduced operating costs through reduced air exchange requirements for the animal production facilities 18, capturing of greenhouses gasses, and capturing of other gasses that are detrimental to the health of the animals or useful for industry. Relative to other systems for capturing biogas 50, the biogas collection apparatus 10 is easier and less expensive to install and to operate, does not significantly increase a footprint of the animal production facility 18, does not require changes to existing waste management systems, and does not typically require permitting for tanks or storage. The biogas collection apparatus 10 thus overcomes many of the barriers for the operators of animal production facilities 18 to enter the biogas market.

The present invention also anticipates a biogas collection system 54, which comprises an animal production facility 18, a biogas processor 24, and a biogas collection apparatus 10, according to the specification above. The animal production facility 18 comprises a slotted floor 56, upon which animals are held, and a waste collection pit 16 positioned beneath the slotted floor 56. The waste collection pit 16 is configured to receive waste 14 that is excreted by the animals upon passage of the waste 14 through the slotted floor 56. The biogas collection apparatus 10 is positioned in the waste collection pit 16 and is operationally engaged to the biogas processor 24. The collectors 26 are configured to collect bubbles 48 of biogas 50 and to direct the biogas 50 through the piping network 20 to the biogas processor 24. The collectors 26 also are configured to allow for passage of waste 14 from the slotted floor 56 into the waste collection pit 16.

In use, the biogas collection apparatus 10 enables a method of collecting biogas 58, which entails provision of the biogas collection apparatus 10, according to the specification above. A first step 60 of the method 58 is positioning the biogas collection apparatus 10 upon the surface of waste 14 in a waste collection pit 16 of an animal production facility 18 so that the piping network 20 is maintained proximate to the surface level 22 of the waste 14 by the floats 12 and such that an open bottom 30 of each collector 26 is positioned below the surface level 22 of the waste 14. A second step 62 of the method 58 is fluidically connecting the piping network 20 to a biogas processor 24. A third step 64 of the method 58 is waste 14 passing through a slotted floor 56 of the animal production facility 18 into the waste collection pit 16. A fourth step 66 of the method 58 is microbial generation of biogas 50 from the waste 14. A fifth step 68 of the method 58 is collecting of bubbles 48 of biogas 50 by the collectors 26. A sixth step 70 of the method 58 is directing of the biogas 50 through the piping network 20 to the biogas processor 24.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:
1. A biogas collection apparatus comprising:

a plurality of floats configured to be positioned upon waste in a waste collection pit of an animal production facility;

a piping network attached to the plurality of floats, wherein the plurality of floats is configured to maintain the piping network proximate to a surface level of waste in the waste collection pit, the piping network being configured for fluidic connection to a biogas processor; and a plurality of collectors attached to and extending from the piping network, such that a closed top of each collector of the plurality of collectors is in fluidic communication with the piping network, such that an open bottom of each collector of the plurality of collectors is positioned below the surface level of the waste, and such that the collectors of the plurality of collectors are arrayed in a plurality of levels, each level of the plurality of levels being positioned at a respective distance below the piping network, each collector in a respective level being positioned over an associated gap defined by adjacently positioned collectors positioned below the collector, wherein each collector of the plurality of collectors is configured to collect bubbles of biogas and to transfer the biogas into the piping network and to allow for passage of waste into the waste collection pit.

2. The biogas collection apparatus of claim 1, wherein the plurality of levels comprises an upper level and a lower level, each collector in the upper level being positioned over the gap defined by the adjacently positioned collectors in the lower level.

3. The biogas collection apparatus of claim 1, wherein each collector of the plurality of collectors comprises an inverted trough.

4. The biogas collection apparatus of claim 3, wherein the inverted trough has a cross-sectional profile, the cross-sectional profile being substantially semicircular.

5. The biogas collection apparatus of claim 2, further including a plurality of cross braces attached to the piping network to stabilize the piping network.

6. The biogas collection apparatus of claim 1, further including an exhaust pipe attached to the piping network and being configured to be connectable to the biogas processor.

7. A biogas collection system comprising:

an animal production facility comprising:

a slotted floor upon which animals are held;

a waste collection pit positioned beneath the slotted floor, wherein the waste collection pit is configured to receive waste excreted by the animals upon passage of the waste through the slotted floor;

a biogas processor; and the biogas collection apparatus of claim 1 being positioned in the waste collection pit and operationally engaged to the biogas processor, such that the collectors of the plurality of collectors collect bubbles of biogas and to direct the biogas through the piping network to the biogas processor, and wherein the plurality of collectors is configured to allow for passage of waste into the waste collection pit.

8. The biogas collection system of claim 7, wherein the plurality of levels comprises an upper level and a lower level, each collector in the upper level being positioned over the gap defined by the adjacently positioned collectors in the lower level.

9. The biogas collection system of claim 7, wherein each collector of the plurality of collectors comprises an inverted trough.

10. The biogas collection system of claim 9, wherein the inverted trough has a cross-sectional profile, the cross-sectional profile being substantially semicircular.

11. The biogas collection system of claim 8, further including a plurality of cross braces attached to the piping network to stabilize the piping network.

12. The biogas collection apparatus of claim 7, further including an exhaust pipe attached to and extending between the piping network and the biogas processor.

13. A method of collecting biogas comprising providing the biogas collection apparatus of claim 1, and:

positioning the biogas collection apparatus upon the surface of the waste in the waste collection pit of an animal production facility, such that the piping network is maintained proximate to the surface level of waste by the plurality of floats and such that an open bottom of each collector of the plurality of collectors is positioned below the surface level of the waste;

fluidically connecting the piping network to a biogas processor; and waste passing through a slotted floor of the animal production facility into the waste collection pit;

microbial generation of biogas from the waste;

collecting of bubbles of biogas by the plurality of collectors; and directing of the biogas through the piping network to the biogas processor.

14. The method of claim 13, wherein the plurality of levels comprises an upper level and a lower level, each collector in the upper level being positioned over the gap defined by the adjacently positioned collectors in the lower level.

15. The method of claim 13, wherein each collector of the plurality of collectors comprises an inverted trough.

16. The method of claim 15, wherein the inverted trough has a cross-sectional profile, the cross-sectional profile being substantially semicircular.

17. The method of claim 14, further including a plurality of cross braces attached to the piping network to stabilize the piping network.

18. The method of claim 13, wherein the step of fluidically connecting the piping network to a biogas processor entails connection of the biogas processor to an exhaust pipe attached to and extending from the piping network.

* * * * *